United States Patent [19]

Uesugi

[11] Patent Number: 5,252,290
[45] Date of Patent: Oct. 12, 1993

[54] PROCESS FOR TREATMENT AND DISPOSAL OF MEDICAL WASTE MATERIALS

[76] Inventor: Jun Uesugi, c/o Pafco Co., Ltd. Gotanda City Heights No. 502, Nishi-Gotanda, 1-29-2, S-inagawa-ku, Tokyo, Japan

[21] Appl. No.: 443,136

[22] Filed: Nov. 30, 1989

[51] Int. Cl.⁵ .................. A61L 2/00; G05B 1/00; G05D 20/00
[52] U.S. Cl. .................... 422/22; 422/5; 422/25; 422/28; 422/32; 422/105; 422/124; 422/294; 422/309; 422/307; 241/23; 241/DIG. 38; 588/258
[58] Field of Search .......... 422/5, 24, 32, 40, 294, 422/309, 22, 28, 307, 23, 105, 124; 206/366, 370; 241/DIG. 38, 23

[56] References Cited

U.S. PATENT DOCUMENTS

| | | | |
|---|---|---|---|
| 2,731,208 | 1/1956 | Dodd | 422/28 |
| 2,895,828 | 7/1959 | Kamide | 426/243 |
| 3,069,734 | 12/1962 | Leuthner | 422/294 |
| 3,721,183 | 3/1973 | Dunlea, Jr. | 422/24 |
| 3,977,091 | 8/1976 | Hortig et al. | 422/40 |
| 4,037,795 | 7/1977 | Fyfe | 241/58 |
| 4,185,973 | 1/1980 | Tester | 55/212 |
| 4,374,491 | 2/1983 | Stortroen et al. | 422/26 |
| 4,552,720 | 11/1985 | Baker, Sr. et al. | 422/295 |
| 4,937,046 | 6/1990 | Andersen et al. | 422/294 |

FOREIGN PATENT DOCUMENTS

| | | | |
|---|---|---|---|
| 2505185 | 8/1976 | Fed. Rep. of Germany | 422/26 |
| 3510830 | 10/1986 | Fed. Rep. of Germany | 422/28 |
| 3604582 | 7/1987 | Fed. Rep. of Germany | 422/32 |
| 3905842 | 9/1989 | Fed. Rep. of Germany | 422/124 |
| 2246805 | 11/1987 | Japan | 422/23 |

OTHER PUBLICATIONS

Tipler, *Physics*, 1976, p. 515.
Brown et al., *Theory and Application of Radio–Frequency Heating*, 1947, p. 17.
Block, Disinfection, Sterilization, and Preservation, 1983, p. 29, 1st col., 1st paragraph.

*Primary Examiner*—Robert J. Warden
*Assistant Examiner*—Theresa A. Trembley
*Attorney, Agent, or Firm*—Staas & Halsey

[57] ABSTRACT

A process and apparatus are provided to treat and dispose of medical waste materials to thereby enhance public heath and social hygiene. The medical waste material is sealed in a suitable nonflammable and long infrared radiation pervious container. The container with the waste material therein is subject to long infrared radiation for a sufficient period of time to heat the waste material to sterilizing temperature levels. The container and the sterilized waste materials are then crushed to reduce the same to granular form to facilitate convenient and safe ultimate disposal. Thus, medical waste materials can be treated and rendered harmless immediately and safely at the place where they are created. Such on-site treatment minimizes the cost involved in ultimate disposal and the potential for human contact with dangerous pathogenic waste.

20 Claims, 4 Drawing Sheets

PROCESS FOR TREATMENT AND DISPOSAL OF MEDICAL WASTE MATERIALS

BACKGROUND OF THE INVENTION

This invention relates to the treatment and disposal of medical waste materials, and more particularly relates to the treatment and disposal of medical waste using nonflammable cartons constructed of specially selected and treated paper materials which are laminated to provide rigidity and leak resistance. The waste materials are sealed in such cartons and the cartons are then heated to sterilize the infectious medical waste contained therein. The cartons and the sterilized materials are then automatically transported to a crusher where the carton and sterilized materials are crushed into a granular form using a motor operated crusher. The invention therefore provides a safe method for treating medical waste on an on-site basis. Focussing on this point, the apparatus of the invention is designed to reduce the weight and volume of institutional solid waste, to sterilize pathogenic waste, to detoxify chemical waste, and to convert noxious waste into innocuous granular particles.

At most institutions, these factors will provide a substantial reduction in off-site disposal costs such that on-site incineration is highly cost-effective. In addition, on-site incineration reduces dependence upon off-site disposal contractors which, in turn, minimizes potential exposure and liability associated with illegal or improper waste disposal activities.

Clearly, the most important factor currently militating toward on-site incineration for healthcare organizations and research institutes across the world relates to effective infectious waste management and disposal. The present invention enables effective on-site incineration using long infrared radiation heater panels and efficient disposal by crushing of the sterilized waste. The processes are carried out automatically and thus direct human involvement is minimized.

For many institutions, particularly hospitals, incineration is the only viable technology available for processing the increased, voluminous quantities of pathogenic waste.

Off-site disposal difficulties and limitations probably contribute the greatest incentives for many healthcare and other institutions to consider or select on-site incineration as the preferred infectious waste treatment method.

SUMMARY OF THE INVENTION

The present invention provides a novel procedure and novel apparatus to address these serious circumstances.

This invention has for an object the provision of a process and related apparatus to sterilize pathogenic waste, to detoxify chemical waste, and to convert noxious waste into innocuous granular shaped refuse.

The present invention has as another object the provision of a process and apparatus facilitating automatic treatment and disposal of medical waste so that human involvement is minimized and humans are protected against exposure to infectious or horrible diseases during handling and transportation.

The invention has as a further object the provision of a process and apparatus to effectively and promptly treat and dispose of medical waste materials without keeping the same for a long period of time.

Other objects and advantages of this invention will become more apparent from the detailed descriptions set forth hereinafter.

This invention provides a process and related apparatus for treatment and disposal of medical waste using a heat-resistant paper box into which medical waste is placed and the box sealed. The box and the waste are heated to a sterilization temperature of 180° C. to 250° C. by long infrared radiation heat panels in a sterilization chamber and the box and sterilized waste materials are pulverized and reduced to refuse in granular form. Thus, the invention enables the pulverization of medical waste including sharp objects and the like and sterilization is carried out using long infrared radiation heater panels while an electric motor operated blower mounted in the upper part of the apparatus provides a flow of air by convection to stabilize the temperature in the chamber and assure effective sterilization. Another electric motor operated blower is provided in the lower portion of the apparatus, to provide a flow of air for conveying crushed waste pneumatically to the final storage area. Ozone is injected into the pneumatic conveying air to dissipate foul odors deriving from the sterilization and residual odors in the crusher unit. Thus, medical waste may be treated automatically with minimal human involvement in the treating process.

DETAILED DESCRIPTION OF THE PREFERRED EMBODIMENTS

Figure 1:
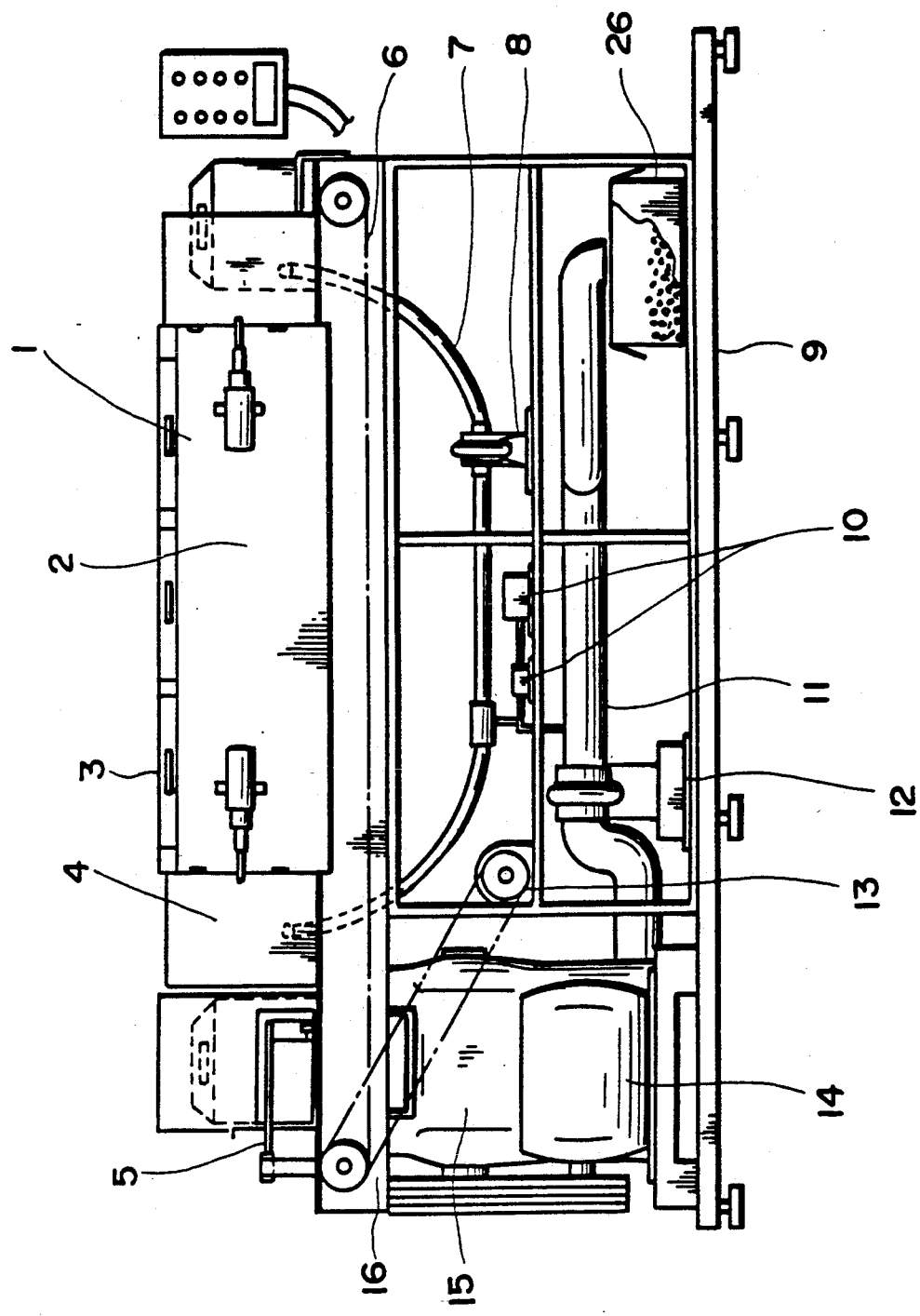
FIG. 1 is a front elevation view of an apparatus which embodies the principles and concepts of the invention.
Figure 2:
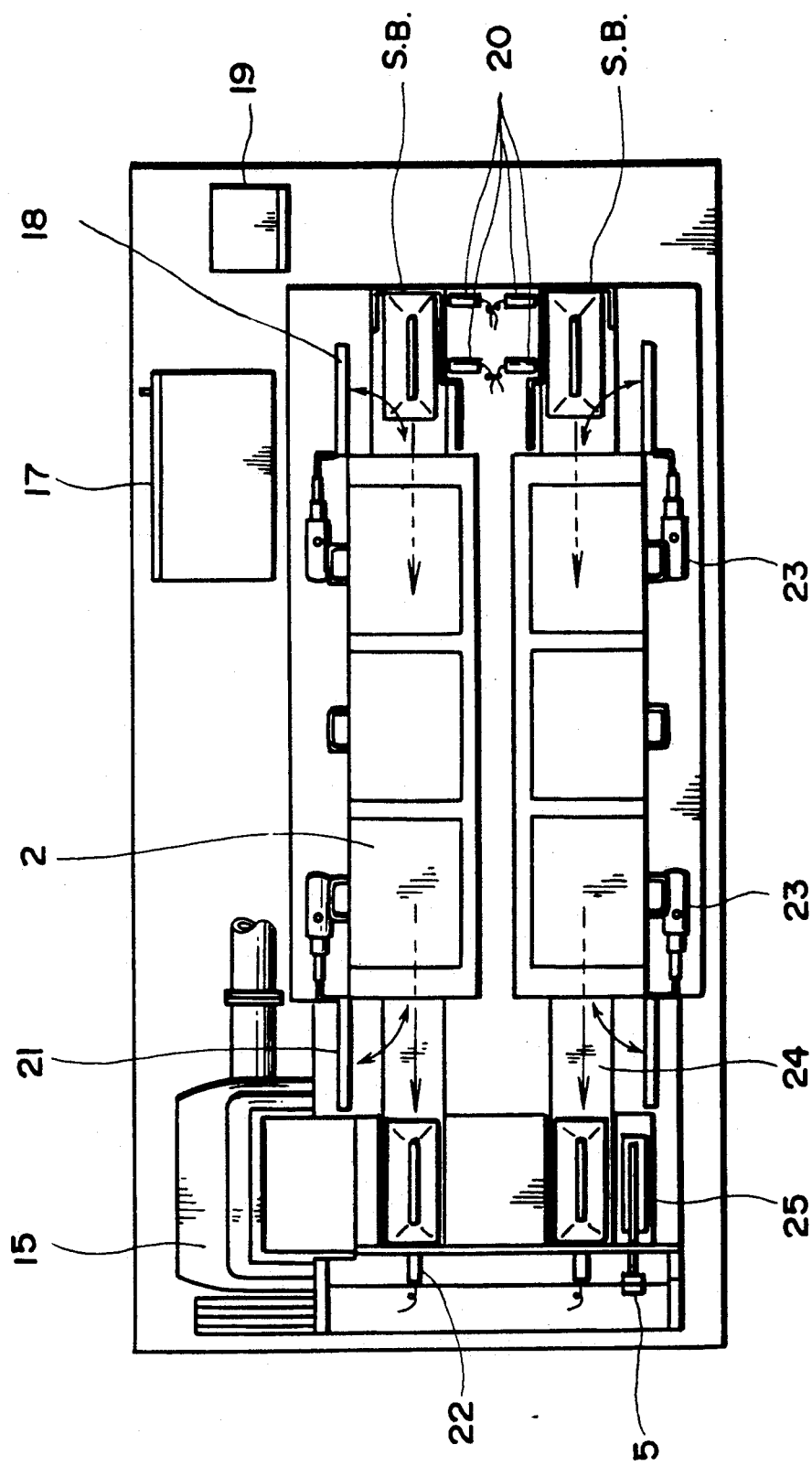
FIG. 2 is a plan view of the apparatus of FIG. 1.
Figure 3:
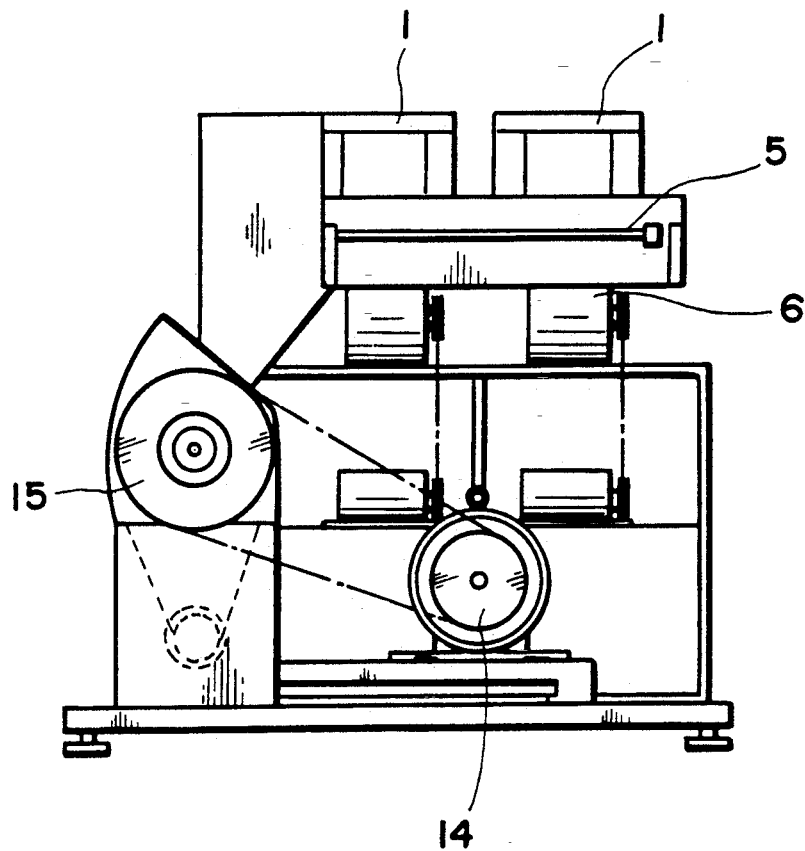
FIG. 3 is a side elevation view of the apparatus of FIG. 1.

An apparatus which embodies the concepts and principles of the present invention is illustrated in FIGS. 1, 2 and 3. With reference to the drawings the apparatus includes a heat sterilizing chamber 1 comprising long infrared heater panels 2, an upper lid 3 and a temperature sensor 4. A linear motor 5 is used to transfer a sterilized carton (shown in dashed lines in FIG. 1) from a belt conveyor and into a crusher 15. A conveyor chain 6 is operated by a conveyor motor 13, and a conveyor guide 16 is positioned beneath conveyor chain 6. A blower 8 connected to a duct 7 causes convective activity in the heat sterilizing chamber 1. Duct 7 operates in cooperation with an exhausting duct 11 connected with a lower blower 12 for dissipating foul odors through the use of ozone injected from an ozone generator 10.

An electric motor 14 drives the crusher 15 and waste materials pulverized by crusher 15 are transported into a storage box 26 through exhausting duct 11. The pulverized, sterilized materials in storage box 26 may be further treated properly for disposal. The various components of the apparatus are mounted on a base 9. A control board 17 is provided for the apparatus, and the chamber 1 includes an inlet door 18 for a carton and an outlet door 21 on the opposite side thereof. A manipulating panel 19 is provided to facilitate manipulation of the entire apparatus from a single position. Detectors 20 and 22 are used to detect and confirm the location of a carton running along the conveyor 24. Cylinders 23 are employed to control the opening and closing of inlet and outlet doors 18 and 21, respectively, and an insertion bracket 25 operates to insert the carton from the conveyor 24 into crusher 15.

As used in the present disclosure the terminology "long infrared radiation" refers to infrared radiation having a wavelength in the range of from about 14,000 Å to about 150,000 Å.

In the drawings, the mark "S.B." is used to designate a specially made nonflammable container box of a type which is known in the prior art. The S.B. box is a nonflammable container box or carton constructed from a paper containing hydrated aluminum. A film is laminated on the inner surface of the box for added strength. The box is known to be rigid, leak resistant and impervious to moisture, and to have strength sufficient to prevent tearing or bursting under normal conditions of use and handling of sharp objects and residual fluids. It also is capable of withstanding leakage of fluids such as blood.

The sharp objects which can be accommodated by the box include objects that have been used in human patient care or treatment or in medical research or in industrial laboratories, including hypodermic needles, syringes (with or without attached needle), pasteur pipettes, scalpel blades, blood vials, needles with attached tubing, and culture dishes (regardless of the presence of infectious agents). Other sharp objects that can be disposed of in the S.B. box include other types of broken or unbroken glassware that have been in contact with infectious agents, such as, for example, used slides and cover slips.

The S.B. box may also be used to dispose of blood and blood products, including such things as liquid waste human blood, products of blood, items saturated and/or dripping with human blood, and items that were once saturated and/or dripping with human blood and that are now caked with dried human blood. The S.B. box is suitable for disposing of serum, plasma, and other blood components, and their containers, which were used or intended for use in patient care, testing and laboratory analysis or in the development of pharmaceuticals. Intravenous bags are also included in this category.

In accordance with the invention the container box must be pervious to long infrared radiation. That is to say it must possess the characteristic of allowing long infrared radiation to pass through its walls. Moreover, the box must be nonflammable in the sense that its physical appearance and condition are preserved while it is subjected to the heating and sterilizing operation in the sterilizing chamber 1 and until it is transported to crusher 15 to undergo the crushing process. Thus, human involvement is not required during the sterilization, transportation and crushing processes. The preferred dimensions of such a container box are 133 mm×300 mm×250 mm.

Figure 4:
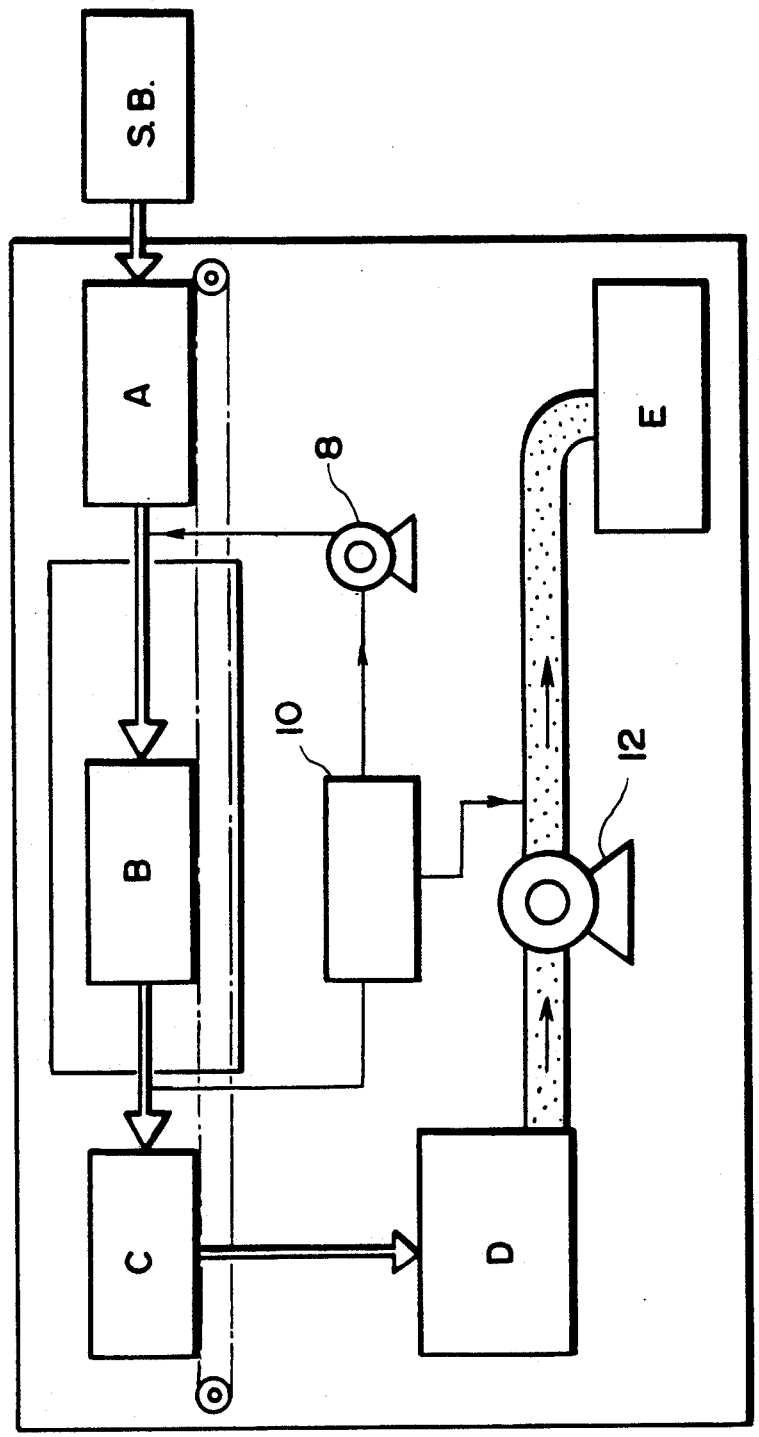
FIG. 4 is a basic block diagram proving a flowchart of the process of a preferred embodiment of the invention.

The process of the invention will now be explained with reference to FIG. 4. When a box S.B. filled with waste material is positioned at the zone identified with the mark "A" (zone A), the operation is initiated by using an appropriate control on panel 19 and inlet door 18 opens and outlet door 21 closes. The presence at zone A of the special carton S.B. containing the medical waste material, which has been appropriately sealed, is automatically sensed by detector 20. The box is then moved toward zone B by conveyor 24.

As the box S.B. is moved toward zone B on conveyor 24 detector 20 provides a sufficient signal to cause conveyor 24 to move in correspondence with the carton size so that the carton becomes positioned at zone B in the heat sterilizing chamber 1. After the carton has moved to zone B in chamber 1, inlet door 18 closes and long infrared radiation heater panels 2 are energized to begin the heat sterilization procedure. The temperature for heat sterilization should be preset in the range of from about 180° C. to about 250° C. A total of 12 heater elements may preferably be installed on the interior walls of the chamber 1, with 6 elements being installed on the right and with 6 elements being installed on the left. During operation the temperature is continuously sensed by a temperature sensor 4 so as to maintain the preset temperature. With regard to the timing of the sterilization operation, it generally will be sufficient to preset the time so that the sterilization proceeds for about one full hours.

During sterilization air is supplied by an upper blower 8 to cause convection to occur in chamber 1. Such convective flow stabilizes the ambient temperature within chamber 1 and serves to eliminate foul odors and smoke produced as a result of the sterilizing procedures. When the preset time passes, outlet door 21 opens and the carton is moved out of chamber 1 and toward zone C by conveyor 24.

When the carton reaches zone C its presence is acknowledged by an appropriate sensor and the conveying movement stops. When the presence of the carton at zone C is confirmed by detector 22, a linear motor operates to push the carton to the entrance of the crusher 15 where the insertion bracket 25 operates to push the carton entirely into crusher 15 until it reaches zone D.

When the box is properly received at zone D, the motor 14 of crusher 15 is energized, and crusher 15 operates to crush and pulverize the box and the medical waste materials therein into granular refuse.

As crusher motor 14 starts to rotate to operate the crusher 15 and initiate the crushing sequence, a lower blower 12 begins to operate to transfer the crushed and pulverized granular waste into a storage box 26 using pneumatic powder flow transportation methodology.

During the foregoing procedures, ozone is generated by an ozone generator 10 to appropriately eliminate and dissipate foul odors and smoke present in the heat sterilizing chamber 1, the exit side of the conveyor 24 and the crusher 15.

The procedures as described above are conducted automatically under the control of appropriate sensors, timers and switches. However, the operation may be conducted manually whereby a single carton can be processed in the same manner. In this regard, the transporting, sterilizing and crushing procedures may be conducted manually.

A timer may be set for a single crushing action so that the crusher 15 is stopped automatically. The crusher may also be stopped manually and arranged such that when the crushing stops the entire apparatus stops simultaneously.

A single action of the heat sterilizer may also be automatically terminated using a preset timer. When the preset time has passed, the outlet door 21 may be opened automatically, and both the upper blower 8 and the lower blower 12 may be energized to eliminate foul odors and smoke. When the appropriate time has gone by the blowers may be deenergized automatically or manually. After these procedures the carton may be extracted by opening the upper lid 3.

During the foregoing procedures, foul odors and smoke may be generated as a result of the heating of the waste material. The odors and smoke may be cleared using the following systems. Upper blower 8 pulls the odorous gas from heat systems. Upper blower 8 pulls the odorous gas from heat sterilizing chamber 1 and transfers the gas into an ejector disposed beneath crusher 15. The waste materials crushed by chamber 15 are transferred to an exhaust duct 11 by the action of lower blower 12. Ozone gas is inserted into the gas streams in the vicinity of the ejector and the ozone reacts with the odorous gas in exhaust duct 11 and in a cyclone dust collector (not shown) resulting in deodorization of the gas. The cyclone collector separates the crushed waste materials from the air. The crushed waste materials are deposited in a sealed container located beneath the cyclone. A level sensor located on the lid of the sealed container senses the level of powder in the container so that appropriate measures can be instituted when the container is full. The deodorized gas, after the remaining ozone therein is dissipated by an ozone trap in the upper part of the cyclone and remaining smoke is removed by a minute filter, is finally dissipated into the air.

The exhaust duct 11 to be used in the described procedures preferably should incorporate a number of design features. Substances with high viscosity such as blood may tend to stick to the inner walls of the duct, and therefore the material from which the duct is constructed should be such that viscous materials do not accumulate in the duct. At places in the duct such as elbows where dust may tend to collect, the shape should be such that the air stream and materials therein flow smoothly at such places. Broken glass and pieces of metal may tend to abrade the inner surfaces of the duct and therefore the duct material should have good durability and the ability to resist such abrasion. Some corrosion may also be caused by ozone gas, and therefore the duct should be constructed using an ozone resistant material.

With regard to the container box or carton to be used in connection with this invention, the ones described above have been developed in the prior art; however, the invention is not limited only to the use of such a box. The important features are simply that the box should be pervious to long infrared radiation and that the heating procedures do not cause damage or disrupt the original form of the box to any substantial extent. The box should also be sturdy enough to keep needles, metal pieces, and broken glass and the like from passing through the wall of the carton during processing. Accordingly, the box, for example, may be constructed of materials resulting from recent ceramic technology, etc.

With regard to the sterilization temperature, the present disclosure describes the same as being based on present academic theories. In this regard, horrible diseases such as A.I.D.S. (Acquired Immune Deficiency Syndrome) and Type B Hepatitis have been reported and shown to be communicable to humans through treatment and handling waste materials. For instance, Hepatitis B Virus is said to become inert after heating at 60° C. for 30 minutes. The World Health Organization, however, requires that such virus should be handled by heating at 121° C. for 30 minutes followed by treatment with ethylene oxide. With reference to the A.I.D.S. virus, present academical research reports that it dies in the air, but it is of course advisable and recommendable that such virus also should be subjected to heating to make sure that the virus is killed in due course.

It is to be understood that the form of this invention as shown and described herein is to be considered to be the preferred form of the same and that various changes in the shape, size and arrangement of parts may be resorted to without departing from the spirit of this invention or the scope of the following claims.

I claim:

1. A process for treatment and disposal of medical waste materials comprising:
   providing a sealable, nonflammable carton constructed of a material pervious to long infrared radiation;
   placing medical waste material in said carton and sealing the same;
   subjecting the exterior of the carton with the medical waste material contained therein to long infrared radiation for a period of time until the medical waste material is sterilized; and
   crushing the carton and the sterilized medical waste material to reduce the same to granular form.

2. A process as set forth in claim 1, wherein the step of subjecting the carton and medical waste material to long infrared radiation is conducted in a sterilizing chamber and said method includes the step of positioning the carton containing the medical waste material in said chamber.

3. A process as set forth in claim 2, wherein is included the step of circulating air in said chamber by convection to stabilize the temperature in the chamber during the period of time that the carton and medical waste are subjected to long infrared radiation.

4. A process as set forth in claim 3, wherein the air circulating in the chamber by convection is utilized to dissipate odor and smoke generated during sterilization of the waste materials.

5. A process as set forth in claim 4, including the step of injecting ozone into the circulating air to dissipate said odor and smoke.

6. A process as set forth in claim 2, wherein long infrared radiation heaters are mounted on interior walls of the chamber.

7. A process as set forth in claim 2, wherein is included the step of sensing the temperature in said chamber to insure the maintenance of a preset sterilization temperature for a predetermined period of time.

8. A process as set forth in claim 1, wherein is included the step of transferring the crushed granular waste materials to a storage box.

9. A process as set forth in claims 8, wherein said transferring the granular waste materials is effected pneumatically using a flow of conveying air.

10. A process as set forth in claim 9, wherein is included the additional step of injecting ozone into said conveying air to dissipate residual odor and smoke carried thereby.

11. A process as set forth in claim 1, wherein said procedures are conducted automatically.

12. A process as set forth in claim 1, wherein said procedures are conducted manually.

13. Apparatus for treatment and disposal of medical waste materials contained in a sealed, nonflammable, long infrared radiation pervious container, said apparatus comprising:

a sterilization chamber including means for subjecting the container and the waste material therein to long infrared radiation for a period of time until the medical waste is sterilized;

crushing means for crushing the container and the sterilized waste material to reduce the same to granular form; and storage means for collecting and storing the granular sterilized waste material.

14. Apparatus as set forth in claim 13, wherein is included first conveyor means for transferring the container and sterilized waste material therein from the chamber to the crushing means and second conveyor means for transferring the crushed granular material from the crusher to the storage means.

15. Apparatus as set forth in claim 13, wherein is included convection means for circulating air in the chamber to stabilize the temperature in the chamber during the sterilization of the waste material.

16. Apparatus as set forth in claim 15, wherein is included means for injecting ozone into the air circulated by the convection means to dissipate smoke and odor generated during said sterilization of the waste material.

17. Apparatus as set forth in claim 13, wherein said sterilization chamber has interior wall surface and said means for subjecting the container and waste material to long infrared radiation includes a plurality of long infrared radiation heater elements mounted on said interior wall surfaces.

18. Apparatus as set forth in claim 13, wherein is included means in the chamber for sensing the temperature therein to insure the maintenance of a preset sterilization temperature for a predetermined period of time.

19. Apparatus as set forth in claim 14, wherein said second conveyor means includes means for generating a flow of air to transport the granular waste material pneumatically from the crusher means to the storage means.

20. Apparatus as set forth in claim 19, wherein said injection means includes means for injecting ozone into the flow of air generated to transport the granular waste material to dissipate any residual odor and smoke carried by said granular waste material.

* * * * *